(12) United States Patent
Everard et al.

(10) Patent No.: US 7,880,881 B2
(45) Date of Patent: Feb. 1, 2011

(54) METHOD OF IMPROVING CHEESE QUALITY

(75) Inventors: Colm D. Everard, Thurles (IE); Donal J. O'Callaghan, White Cross (IE); Colm P. O'Donnell, Consicegh (IE); Colleen C. Fagan, Giasnevin (IE); Manuel Castillo, Lexington, KY (US); Frederick Alan Payne, Lexington, KY (US)

(73) Assignee: University of Kentucky Research Foundation, Lexington, KY (US)

( * ) Notice: Subject to any disclaimer, the term of this patent is extended or adjusted under 35 U.S.C. 154(b) by 808 days.

(21) Appl. No.: 11/789,197

(22) Filed: Apr. 24, 2007

(65) Prior Publication Data

US 2008/0270063 A1    Oct. 30, 2008

(51) Int. Cl.
*G01J 3/46* (2006.01)
(52) U.S. Cl. .......................... 356/402; 426/34; 426/36; 426/582
(58) Field of Classification Search ................. 356/300, 356/303, 317; 702/108; 426/34, 36, 580, 426/582, 231–233, 248
See application file for complete search history.

(56) References Cited

U.S. PATENT DOCUMENTS

| | | | |
|---|---|---|---|
| 2,752,815 A | 7/1956 | Batchelor | |
| 4,144,804 A | 3/1979 | O'Keefe et al. | |
| 4,359,638 A | 11/1982 | Allport | |
| 4,497,898 A | 2/1985 | Anderson et al. | |
| 4,521,433 A | 6/1985 | Linklater et al. | |
| 4,542,645 A | 9/1985 | Richardson et al. | |
| 4,986,660 A | 1/1991 | Corbett | |
| 5,009,794 A | 4/1991 | Wynn | |
| 5,137,738 A | 8/1992 | Wynn | |
| 5,172,193 A | 12/1992 | Payne et al. | |
| 5,273,765 A | 12/1993 | Weber | |
| 5,403,552 A | 4/1995 | Pardikes | |
| 5,751,424 A | 5/1998 | Bostater, Jr. | |
| 5,912,730 A | 6/1999 | Dahm et al. | |
| 5,955,128 A | 9/1999 | Bayevsky et al. | |
| 5,983,709 A | 11/1999 | O'Keeffe | |
| 6,052,184 A | 4/2000 | Reed | |

(Continued)

FOREIGN PATENT DOCUMENTS

FR    2680079 A1    2/1993

OTHER PUBLICATIONS

Castillo et al., Optical sensor technology for measuring whey fat concentration in cheese making, Journal of Food Engineering, 71 (2005) 354-360.*

(Continued)

*Primary Examiner*—Tarifur Chowdhury
*Assistant Examiner*—Abdullahi Nur
(74) *Attorney, Agent, or Firm*—King & Schickli, PLLC

(57) ABSTRACT

A method is provided for improving the quality of cheese produced from a curd and whey mixture. The method comprises the steps of monitoring the curd and whey mixture during syneresis processing to collect color data, comparing the color data to a predetermined standard and terminating syneresis when the color meets the predetermined standard or, alternatively, analyzing the color data obtained to generate kinetic parameters that can be used to predict the end point of syneresis to improve control of curd moisture content.

12 Claims, 2 Drawing Sheets

U.S. PATENT DOCUMENTS

| | | | |
|---|---|---|---|
| 6,111,653 | A | 8/2000 | Bucknell et al. |
| 6,147,502 | A | 11/2000 | Fryer |
| 6,315,955 | B1 | 11/2001 | Klein |
| 6,458,394 | B1 * | 10/2002 | Talbott .................... 426/36 |
| 6,721,054 | B1 | 4/2004 | Spooner |
| 6,753,966 | B2 | 6/2004 | Von Rosenberg |
| 6,795,183 | B2 | 9/2004 | O'Keeffe |
| 6,831,741 | B1 | 12/2004 | De Kruif et al. |
| 6,836,325 | B2 | 12/2004 | Maczura |
| 6,963,403 | B2 | 11/2005 | Nagarajan et al. |
| 6,992,771 | B2 | 1/2006 | Bond et al. |
| 7,092,084 | B2 | 8/2006 | Payne |
| 7,217,234 | B2 | 5/2007 | Zettier |
| 2003/0030809 | A1 | 2/2003 | Boas |
| 2003/0098969 | A1 | 5/2003 | Katz et al. |
| 2005/0233037 | A1 | 10/2005 | Bendtsen et al. |
| 2006/0044558 | A1 | 3/2006 | Furukawa |
| 2006/0057249 | A1 | 3/2006 | Bell et al. |
| 2007/0014893 | A1 | 1/2007 | Misson et al. |
| 2008/0268110 | A1 | 10/2008 | Castillo et al. |
| 2009/0255473 | A1 | 10/2009 | Katz et al. |

OTHER PUBLICATIONS

Syneresis Sensor technology development for curd moisture content control. Second Annual Kentucky Innovation and enterprise Conference, Lexington, USA, Mar. 3, 2004.*

Castillo, M., Payne, F.A., Lopez, M.B., Ferrandini, E., Laencina, J. 2005. Preliminary Evaluation of an Optical Method for Modeling the Dilution of Fat Globules in Whey During Synergesis of Cheese Curd. Applied Engineering in Agriculture, vol. 21(2): 265-269.

Castillo, M., Payne, F.A., Fagan, C.C., Leedy, M., O'Donnell, C.P., O'Callaghan, D.J., Feb. 2006. Backscatter of Near Infrared Light as an Instrument to Improve Control of Curd Moisture Content During Cheese Manufacturing. International Scholar Poster Session. Poster. Department of Biosystems and Agricultural Engineering, University of Kentucky.

Castillo, M., Payne, F.A., Mengue, M.P., Mar. 30, 2005. Simultaneous Monitoring of Coagulation and Syneresis in Cheese Processing Using Light Backscatter. Third Annual Kentucky Innovation and Enterprise Conference. Poster. Louisville, Kentucky, USA.

Castillo, M., Payne, F.A., Mengue, M.P., Leedy, M.A. Feb. 24, 2005. Novel Optical Sensor Technology for Simultaneous Monitoring of Coagulation and Syneresis in Cheese Processing. Poster. Lexington, Kentucky, USA.

Castillo, M., Payne, F.A., Mengue, M.P. Mar. 3, 2004. Syneresis Sensor Technology Development for Curd Moisture Content Control. Second Annual Kentucky Innovation and Enterprise Conference. Poster. Lexington, Kentucky, USA.

Castillo, M., Payne, F. A., Mengue, M.P. Apr. 14, 2004. Large Field of View Light Backscatter Sensor for Monitoring Whey Syneresis and Control Curd Moisture Content. Second International Scholar Poster Session. Poster. Lexington, Kentucky, USA.

Castillo, M., Payne, F., Lopez, M.B., Ferrandini, E., Laencina, J., 2004. Kinetics of Synerisis During Goats' Cheese Manufacturing. In Actas del 9th International Congress on Engineering and Food.

Castillo, M., Payne, F., Lopez, M.B., Ferrandini, E., Laencina, J. 2004. Development of a Fiber Optic Sensor to Measure Low Fat Concentration in Goats' Whey. In Actas del 9th International Congress on Engineering and Food.

Castillo, M., Payne, F.A., Lopez, M.B., Laencina, J. 2005. Optical Sensors to Monitor and Control the Processing of Goat Cheese. in Special Issue of Dairy Federation 0501/Part 4; pp. 250-256. Ed. International Dairy Federation.

Castillo, M., payne, F.A., Shea, A. Jul. 24-28, 2005. Development of a Combined Sensor Technology for Monitoring Coagulation and Syneresis Operations in Cheese Making. ADSA Annual Meeting. Poster. Cincinnati, Ohio, USA.

Everard, C.D., O'Callaghan, D.J., Fagan, C.C., O'Donnell, C.P., Castillo, M., Payne, F.A., Reflection photometry and physico-chemical measurements to monitor cheese curd syneresis. 36th Annual Research Conference. Food, Nutrition and Consumer Sciences. Poster. Cork, Ireland, Sep. 14, 2006.

Everard, C.D., O'Donnell, C.P., Fagan, C.C., O'Callaghan, D.J., Castillo, M., Payne, F.A.. Application of computer vision to control curd and whey quality during cheese syneresis. EFFoST Annual Meeting/ Total Food, The Hague, The Netherlands, Nov. 7-9, 2006.

Everard, C.D., O'Donnell, C.P., Fagan, C.C., O'Callaghan, D.J., Castillo, M. Payne, F.A.. Computer vision analysis to monitor syneresis of cheese curd in a cheese vat. ADSA-ASAS Annual Meeting, Minneapolis, Minnesota, USA, Jul. 9-13, 2006.

Office Action U.S. Appl. No. 12/109,650 Oct. 20, 2010.

Lamb et al. "Milk protein denaturation indicated by light scatter analysis" Poster presentation, ASABE International Annual Meeting, Providence, RI, 2008.

* cited by examiner and schematical view showing an apparatus for color measurement and conducting the method of the present invention;

METHOD OF IMPROVING CHEESE QUALITY

This invention was made with at least partial Government support under USDA-NRI Grant Nos. 2005-35503-15390 and 2008-35503-18858. The Government may have certain rights in this invention.

TECHNICAL FIELD AND INDUSTRIAL APPLICABILITY OF THE INVENTION

The present invention generally relates to the cheese making art and, more particularly, to a method of improving the quality of cheese produced from a curd and whey mixture.

BACKGROUND OF THE INVENTION

The first major step in the cheese making process is the coagulation of the milk by enzymatic hydrolysis of κ-casein. To achieve this end, enzyme extracts from calf stomachs, microbialy produced enzymes or other enzymes are utilized. The hydrolysis of κ-casein leads to destabilization of the colloidal system of the milk. This is followed by aggregation of the micelles into clusters. Over time, the clusters grow in size. This growth in size is followed by cross-linking between chains which eventually transform the milk into a gel or coagulum. Once a desired point is reached in the coagulation process, the coagulum is "cut" by traversing with wire knives to slice the coagulum into approximately 0.7 cm cubes.

Syneresis is the phase separation process in cheese making that follows the cutting of the milk coagulum into cubes. Syneresis is generally promoted by thermal and/or mechanical treatments. During syneresis, rearrangement of casein network, constituting the gel matrix, causes the shrinkage of the curd matrix and results in expulsion of whey from the curd grains.

Syneresis control influences cheese quality and yield as a result of its effects on moisture, mineral and lactose content of the curd. Syneresis also influences protein and fat loses in whey, which in turn affects cheese yield.

Despite its importance, syneresis is one of the least understood phases in the cheese making process, especially from both a physical/chemical and kinetic prospective. The kinetics of curd syneresis is complex and there are no technologies currently available for monitoring it. At present, in the cheese industry worldwide, syneresis is empirically controlled by vat temperature, milk pH, stirring speed and time, depending on cheese type and the cheese maker's preferences. Inadequate curd moisture control will lead to heterogeneous cheese ripening and quality. Better control of syneresis would give more consistent curd moisture content and pH, and more consistent curd concentration of minerals and lactose at the beginning of the curing process.

It has been found that syneresis is a first order kinetics reaction. As a consequence, one can predict the syneresis end point with some confidence.

The present invention relates to a method of improving the quality of cheese produced from a curd and whey mixture. More specifically, the present method provides improved syneresis control to ensure moisture content consistency and better cheese quality.

SUMMARY OF THE INVENTION

In accordance with the purposes of the present invention as described herein, a method is provided of improving the quality of cheese produced from a curd and whey mixture. The method comprises the steps of monitoring the curd and whey mixture during the syneresis process in order to collect color data, comparing the color data to a predetermined standard and terminating syneresis when the color meets the predetermined standard. A second approach is obtaining kinetic information from collected color data to estimate the kinetics of the syneresis process and predict the time required for the curd to reach the desired curd moisture level.

The monitoring step may include directing light from an incident light source onto a surface of the curd and whey mixture and detecting light reflected from that surface. The method may include using an optical detector to detect the reflected light. The optical detector may be selected from a group of devices consisting of a calorimeter, a CCD camera, a photodetector, or a fiber optic spectrometer.

The method may further include optically distinguishing the curd and whey in the curd and whey mixture. The method may further include determining the degree of syneresis based upon the curd and whey ratio detected in the curd and whey mixture. Still further the method may include stirring the curd and whey mixture with a stirrer during monitoring and collecting color data of the curd and whey mixture while making certain that the stirrer is in precisely the same position so as to not affect the color readings.

Alternatively, the method may be broadly defined as comprising the steps of monitoring the curd and whey mixture during the syneresis process to collect color data and analyzing the color data using computer vision analysis. More specifically, the method may include using an equation for analyzing the color data to provide a computer vision metric $\Delta E_{RGB}$ as a function of time where the equation comprises:

$$\Delta E_{RGB} = \sqrt{(\Delta R)^2 + (\Delta G)^2 + (\Delta B)^2}$$

where $\Delta R$=change in red value, $\Delta G$=change in green value and $\Delta B$=change in blue value.

In accordance with yet another aspect of the present invention the method may be broadly defined as comprising the steps of monitoring the curd and whey mixture during the syneresis process to collect color data and analyzing the color data using colorimetric analysis. More specifically, the method may include using an equation for analyzing the data to provide a color difference value D versus time where the equation comprises: $D = \sqrt{(L_o - L_t)^2 + (a_o - a_t)^2 + (b_o - b_t)^2}$. where $L_o$=lightness variable at time zero, $L_t$=lightness variable at time t, $a_o$=redness/greenness ate time zero, $a_t$=redness/greenness at time t, $b_o$=yellowness/blueness at time zero and $b_t$=yellowness/blueness at time t.

In the following description there is shown and described several preferred embodiments of this invention simply by way of illustration of some of the modes best suited to carry out the invention. As it will be realized, the invention is capable of other different embodiments and its several details are capable of modification in various, obvious aspects all without departing from the invention. Accordingly, the drawings and descriptions will be regarded as illustrative in nature and not as restrictive.

BRIEF DESCRIPTION OF THE DRAWINGS

The accompanying drawings incorporated in and forming a part of the specification, illustrate several aspects of the present invention, and together with the description serve to explain certain principles of the invention. In the drawing.

Reference will now be made in detail to the present preferred embodiments of the invention.

DETAILED DESCRIPTION OF INVENTION

Figure 1:
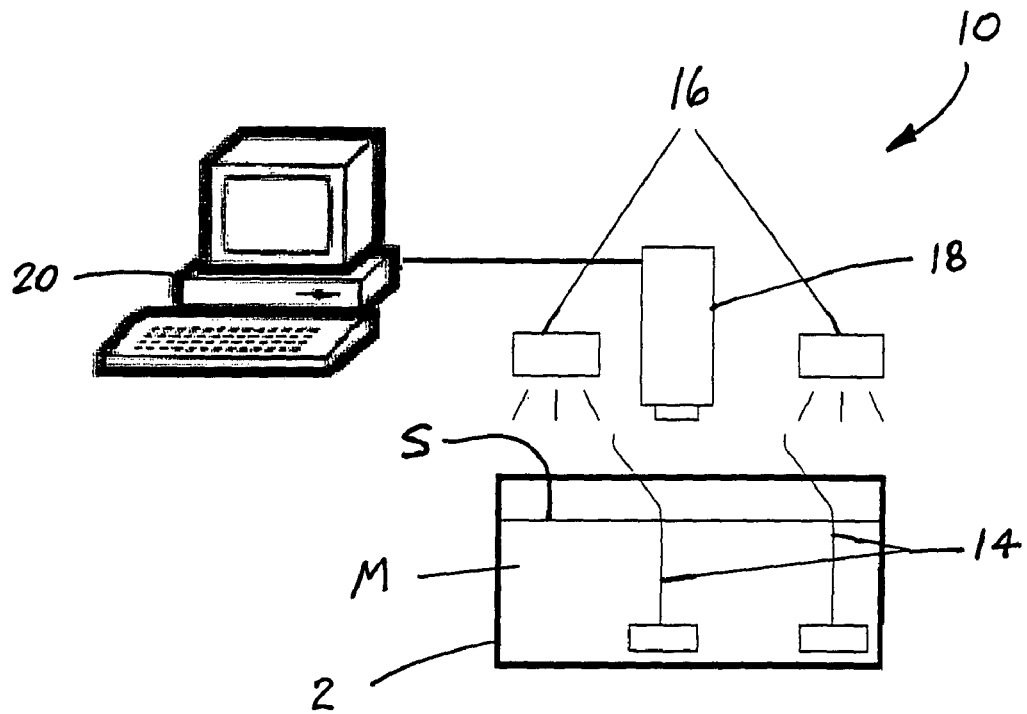
FIG. 1 is a combined partially sectional, side elevational

A computer vision apparatus 10 useful in the present method of improving the quality of cheese produced from a curd and whey mixture is illustrated in FIG. 1. The apparatus 10 includes a vessel or vat 12 for holding a curd and whey mixture M. Mechanical stirrers 14 are provided to stir the mixture M and are rotated at a selected speed. The apparatus 10 further includes a light source, illustrated in the drawing figure as two fluorescent light sources 16, for directing incident light onto the surface S of the curd and whey mixture M. In addition the apparatus includes an optical detector 18. In FIG. 1 the optical detector is illustrated as a CCD camera. It should be appreciated, however, that the optical detector may alternatively comprise a colorimeter, photodetector, a fiber optic spectrometer and combinations thereof. The optical detector 18 is connected to a processor 20 such as a personal computer. The processor 20 compares the color data collected by the optical detector 18 to a predetermined standard or extracts kinetic information about syneresis in order to indicate the proper point for terminating syneresis so as to consistently provide a high quality cheese product.

The present method of improving the quality of cheese produced from a curd and whey mixture may be generally described as comprising the steps of monitoring the curd and whey mixture M as the mixture undergoes the syneresis process in order to collect the color data. This is done by directing light from the incident light source 16 onto the surface S of the curd and whey mixture M and detecting light reflected from the surface of the curd and whey mixture using the optical detector 18. The color data may be collected continuously or, more typically, at predetermined intervals. The collected color data is then stored in a memory device. The processor 20 is then used to compare the collected data to color data for the predetermined standard which is also stored in a memory device. This is followed by terminating 'syneresis' when the collected color data meets the predetermined standard.

In one possible embodiment, the method includes optically distinguishing the curd and whey present in the curd and whey mixture M. In this embodiment the method may further include determining the degree of syneresis of the curd and whey mixture M based upon the curd and whey ratio detected in the curd and whey mixture by the apparatus 10. More specifically, the relatively white area of the curd and whey mixture is the curd while the relatively yellow area of the curd and whey mixture is the whey. The differences in the color of the curd and whey allow the apparatus 10 to detect and establish the curd to whey ratio.

During syneresis the curd and whey mixture M is being stirred. Accordingly, stirring takes place during monitoring and the collection of color data. In order to ensure a proper baseline and minimize interference from the stirrers in obtaining accurate color readings, the method includes the step of collecting color data of the curd and whey mixture by capturing each image at the same stirrer position or an alternative system to eliminate this interference.

The following examples are presented to further illustrate the invention, but it is not to be considered as limited thereto.

EXAMPLE 1

A computer vision system was coupled to a 10 L cheese vat, as shown in FIG. 1 to measure color changes in the curd/whey mixture during syneresis. In this way it was possible to identify the end point of syneresis from color data signal processing to control syneresis and improve cheese quality.

The computer vision system used in this study consisted of a high-quality 3-CCD Sony XC-003P camera (Sony Corporation, Tokyo, Japan) connected to a computer for image analysis with an IC-RGB frame grabber (Imaging Technology, Billerica, Mass.). Images were captured under two fluorescent lamps (Imaging Technology, Billerica, Mass.) with plastic light diffusers. The camera captured images (~100 $mm^2$) of the surface of the curd/whey mixture after curd cutting during syneresis while the mixture was being stirred. Images were captured at t=5 or 6 min (relative to the start of cutting, which took 2-3 min) and at 1 min intervals thereafter up to t=85 min. Care was taken to capture each image at the same stirrer position. RGB values averaged across each successive image were recorded and used to follow syneresis (see Technique A below). The areas of white ($A_w$) and yellow ($A_y$) in each image were determined mathematically from the pictures and their ratio ($a_{wy}=A_w/A_y$) was calculated and used as a parameter to follow syneresis (see technique B below).

As indicated above, the collected color data was analyzed using two different techniques.

Technique A involves analysis of the color content of a series of RGB images of the stirred curd and whey mixture M.

Using MatLab the file was read in and cropped to allow for analysis of the image area of interest i.e. removal of vat walls from the image etc. MatLab was then used to calculate the average RGB values for each image. RGB values averaged across each successive image were recorded and used to follow syneresis.

Figure 2A:
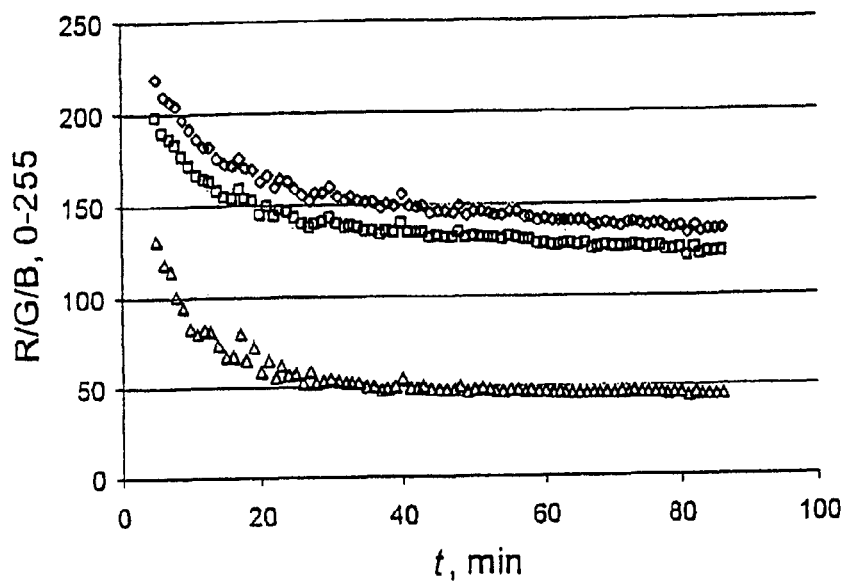
FIG. 2a is a plot of a typical profile for $\Delta E_{RGB}$ as a function of Syneresis time.

The resulting RGB values, i.e. at one-minute intervals, were used to calculate $\Delta E_{RGB}$ using the Euclidean formula Eq. (1), to give a computer vision metric as a function of time with respect to the initial image captured at t=5 min or 6 min $$\Delta E_{RGB} = \sqrt{(\Delta R)^2 + (\Delta G)^2 + (\Delta B)^2} \qquad (Eq. 1)$$

where $\Delta R$ is the change in the R value, $\Delta G$ is the change in the G value and $\Delta B$ is the change in the B value, relative to the RGB value at t=5 min. Note that Eq. (1) is not an equator for color difference per se, but could be considered analogous to color difference in a computer vision sense. Typical profiles for $\Delta E_{RGB}$ as a function of syneresis time are shown in FIG. 2a.

Figure 2B:
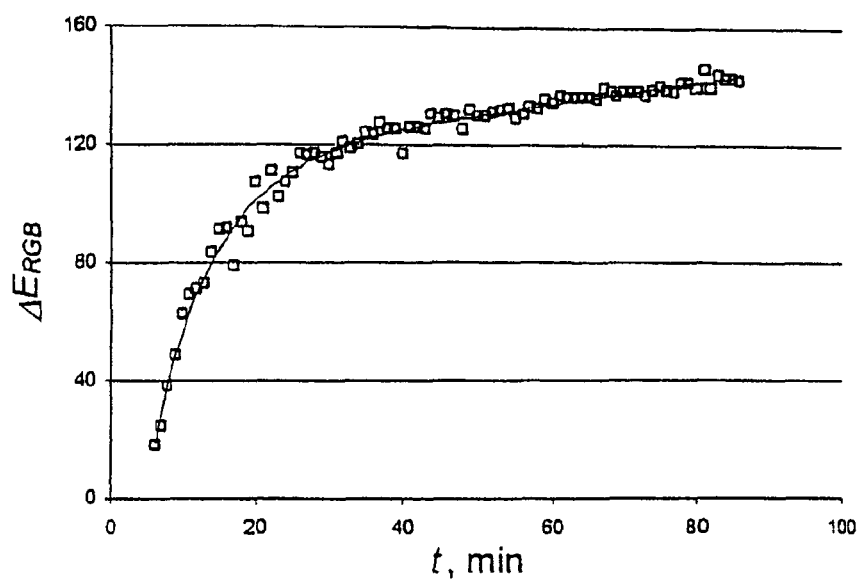
FIG. 2b is a plot illustrating the optimization of the coefficients $\Delta E_0$, $k_1$, $\tau$ and $k_2$ to give a least square fit to $\Delta E_{RGB}$.

A 4-parameter nonlinear model ($\Delta E_M$; Eq. 2) was fitted to $\Delta E_{RGB}$ as a function of time, t, after initiating cutting of the coagulum.

$$\Delta E_M = \Delta E_0[1 - e^{k_1(1-\tau)}] + k_2 t \qquad (Eq. 2)$$

where $k_1$ has a negative value. The coefficients $\Delta E_0$, $k_1$, $\tau$ and $k_2$ were optimized to give a least squares fit to $\Delta E_{RGB}$ as shown in FIG. 2b. The parameters $k_1$ and $k_2$ are considered parameters which measure the kinetics of syneresis.

Technique B involved subdivision of each image into areas of curd or whey, respectively, according to a color threshold.

The RGB (red green blue) threshold between curd (white) and whey (yellow) colors was defined by human perception.

The file was read into MatLab and cropped to allow for analysis of the image area of interest i.e. removal of vat walls from the image etc. The cropped image was then converted into a grayscale image. The grayscale image was de-noised using a two-dimensional adaptive noise-removal filter (Lim, 1990). Following noise-removal, the contrast of the image was enhanced using contrast-limited adaptive histogram equalization (Mathworks, 1998). A threshold value between curd (white) and whey (yellow) colors was defined by human perception to ensure clear separation of the curd and whey. This threshold value was set at 100. A pixel with a value greater than the threshold was given a value of 1 and a pixel with a value less than the threshold was assigned the value 0. The yellow area (whey) was calculated as the sum of pixels with a value greater than the threshold. The white area (curd) was calculated as the total number of pixels minus the yellow area. The areas of white ($A_w$) and yellow ($A_y$) in each image were summed mathematically and their ratio ($a_{wy}=A_w/A_y$) was calculated and used as a parameter to follow syneresis.

Figure 3:
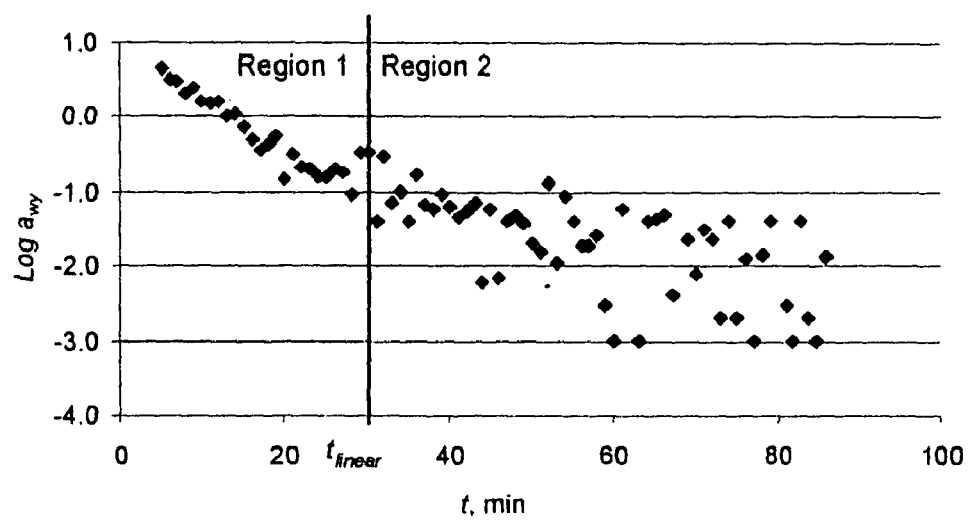
FIG. 3 is a graph of log $a_{wy}$ (log of ratio between white and yellow areas) versus time after cutting the coagulum for a typical trial, using the computer vision apparatus and showing that log $a_{wy}$ decreases in a linear manner up to $t_{linear}$, the vertical bar indicating the point of departure from linear behavior. The slope of the line is correlated to the first order kinetics if syneresis.

Analysis of $a_{wy}$: It was found that the graph of log $a_{wy}$ versus time had two distinct regions and such a graph could be used to derive a parameter, $t_{linear}$, which could be useful in predicting an end-point of syneresis (see FIG. 3). In addition, syneresis kinetic parameters can be obtained from the graph and used in prediction equations to predict the end point of syneresis.

The first region showed a linear decrease in log $a_{wy}$ with time ending at $t_{linear}$. The linear period of time, $t_{linear}$, decreased by ~25-35% due to increased stirring speed, i.e. more rapid stirring implies increased shear velocities on curd surfaces preventing formation of sediment on the curd layer and causes increased collision between curd particles, which speed up syneresis.

The second region of the graph showed a less-defined change in log $a_{wy}$ over time and also showed considerable data scatter. Thus, log $a_{wy}$ could be modeled in the form: log $a_{wy}=y=mt+b$, from t=5 min to $t_{linear}$ (Eq. 3) where the slope m has a negative value and intercept b has a value between 0.5 and 1; log $a_{wy}=y=c$, from t=$t_{linear}$ to 85 min (Eq. 4) (i.e. at t>$t_{linear}$ there is no significant change in log $a_{wy}$).

It was found that the variability in the data (e.g. in the plot of $a_{wy}$ v. time) could be reduced substantially by means of a weighted averaging technique. $a_{wy}$ values were averaged over 5 minutes, i.e. by taking 5 successive values at 1-minute intervals, rearranging them in ascending rank order and applying weights of 8, 4, 2, 1 and 0, respectively, to the five values in the ascending order. One might refer to this algorithm as a weighted average in favour of the lower values in any 5-minute period. The effect of such an algorithm is to minimize errors caused when large individual pieces of curd randomly approach the area of detection.

EXAMPLE 2

Colorimetric analysis involved the use of the colorimeter to record color measurements of the surface of the curd/whey mixture at t=5.5 min and at 1 min intervals thereafter up to t=85.5 min. A hand held tristimulus colorimeter (CR-300, Minolta Limited) with an angle of observation of 0° and an 8 mm diameter field of view, was used. Color measurements were performed using a CIE standard "C" illuminant and were recorded in "Hunter Lab" format, i.e. lightness variable L and chromaticity coordinates a (redness/greenness) and b (yellowness/blueness).

Lab data for the calorimeter were filtered using an algorithm that took a weighted average over 5 min intervals, weighted in favour of the smallest values, i.e. weights 4, 4, 2, 1 and 0 were applied to the five values having been ranked in ascending order. An example will illustrate this:

In a particular case, the values of L, a and b at 5 succeeding time-points where as in Table 1:

TABLE 1

Example of a typical five minutes data set.

| Time, min | L | a | b |
| --- | --- | --- | --- |
| 5 | 48.89 | −6.38 | 12.88 |
| 6 | 76.92 | −7.79 | 9.29 |
| 7 | 64.39 | −6.93 | 10.53 |
| 8 | 58.73 | −5.96 | 7.94 |
| 9 | 47.6 | −6.16 | 9.96 |

L, a and b values are sorted in increasing order of magnitude, and weights 4, 4, 2, 1 and 0, respectively, are applied, as in Table 2, giving weighted mean values L", a" and b" for the median time (7 min in this case) as in Table 3.

TABLE 2

Example of the weighted average procedure.

| L | a | b | Weight |
| --- | --- | --- | --- |
| 47.6 | −5.96 | 7.94 | 4 |
| 48.89 | −6.16 | 9.29 | 4 |
| 58.73 | −6.38 | 9.96 | 2 |
| 64.39 | −6.93 | 10.53 | 1 |
| 76.92 | −7.79 | 12.88 | 0 |

TABLE 3

Averaged Values

| Time, min | $L_t$ | $a_t$ | $b_t$ |
| --- | --- | --- | --- |
| 7 | 51.6 | −6.2 | 9.0 |

The $L_t a_t b_t$ data at each time-point (from t=15 min to t=75 min) were converted into a color difference value (D; Eq. 5) versus time, where D was calculated relative to a reference color ($L_0 a_0 b_0$) for each image captured. The color of milk before enzyme addition was taken as the reference.

$$D=\sqrt{(L_0-L_t)^2+(a_0-a_t)^2+(b_0-b_t)^2} \quad \text{(Eq. 5)}$$

A 4-parameter model (Dm; Eq. 6) was then fitted to a graph of a Lab metric $$D_M=D_0[1-e^{k_3(t-\tau)}]+k_4 t \quad \text{(Eq. 6)}$$

where coefficients $D_0$, $k_3$, $\tau$, $k_4$ were estimated to give a least squares fit to D values at time t after cutting the coagulum. Because the coefficients $D_0$, $k_3$, $\tau$, $k_4$ measure directly the change in syneresis kinetics, they may be used to prediction the end point of syneresis.

In summary, numerous benefits result from employing the concepts of the present invention. More specifically, two embodiments of methods are disclosed for syneresis monitoring in a cheese vat based on color measurement. The first uses computer vision to distinguish curd from whey and the monitoring of color changes in a cheese vat during syneresis. By comparing the collected colored data to a predetermined standard for a cheese of desired consistency, moisture content and quality, it is possible to consistently produce a high quality cheese product. Alternatively, the collected color data may be analyzed to generate kinetic parameters for syneresis. Thus parameters may then be used to predict a syneresis end point to improve control of curd moisture content and, ultimately, cheese quality.

The invention has been described herein with reference to certain preferred embodiments. However, as obvious variations thereon will become apparent to those skilled in the art, the invention is not to be considered as limited thereto.

What is claimed:

1. A method of improving quality of cheese produced from a curd and whey mixture, comprising:
    monitoring said curd and whey mixture using an optical detector during syneresis processing to collect color data;
    comparing said color data to a predetermined standard; and
    terminating syneresis when said color data meets said predetermined standard.

2. The method of claim 1, wherein said step of monitoring to collect color data includes directing light from an incident light source onto a surface of said curd and whey mixture and detecting light reflected from said surface of said curd and whey mixture with said optical detector.

3. The method of claim 1, including selecting said optical detector from a group of devices consisting of a colorimeter, a CCD camera, a photodetector, a fiber optic spectrometer and combinations thereof.

4. The method of claim 1, including optically distinguishing curd and whey in said curd and whey mixture.

5. The method of claim 4, including determining degree of syneresis based upon curd and whey ratio detected in said curd and whey mixture.

6. The method of claim 1, including stirring said curd and whey mixture with a stirrer during monitoring.

7. The method of claim 6, including collecting color data of said curd and whey mixtures by capturing each image when said stirrer is in a particular position.

8. A method of improving quality of cheese produced from a curd and whey mixture, comprising:
    during the syneresis process, monitoring said curd and whey mixture using an optical detector to collect color data;
    analyzing said color data using computer vision analysis; and
    terminating syneresis when said color data meets a predetermined color standard.

9. The method of claim 8, including using an equation for analyzing said data to provide a computer vision metric $\Delta E_{RGB}$ as a function of time, said equation comprising:

$$\Delta E_{RGB} = \sqrt{(\Delta R)^2 + (\Delta G)^2 + (\Delta B)^2}$$

where
$\Delta R$ = change in red value
$\Delta G$ = change in green value
$\Delta B$ = change in blue value.

10. A method of improving quality of cheese produced from a curd and whey mixture, comprising:
    during the syneresis process, monitoring said curd and whey mixture using an optical detector to collect color data;
    analyzing said color data using colorimetric analysis; and
    terminating syneresis when said color data meets a predetermined color standard.

11. The method of claim 10, including using an equation for analyzing said data to provide a color difference value D versus time, said equation comprising:

$$D = \sqrt{(L_o - L_t)^2 + (a_o - a_t)^2 + (b_o - b_t)^2}$$

where
$L_o$ = lightness variable at time 0
$L_t$ = lightness variable at time t
$a_o$ = redness/greenness at time 0
$a_t$ = redness/greenness at time t
$b_o$ = yellowness/blueness at time 0
$b_t$ = yellowness/blueness at time t.

12. A method of improving quality of cheese produced from a curd and whey mixture, comprising:
    using an optical detector, monitoring a curd and whey mixture during syneresis to collect color data;
    analyzing said collected color data to generate kinetic parameters; and
    using said kinetic parameters to predict a syneresis end point to improve control of curd moisture content.

* * * * *